US00PP09604P

United States Patent [19]

Skotak, Jr.

[11] Patent Number: Plant 9,604

[45] Date of Patent: Jul. 9, 1996

[54] NEOREGELIA PLANT NAMED 'NONIS'

[75] Inventor: Chester Skotak, Jr., Alajuela, Costa Rica

[73] Assignee: Dura Flor S.A., Alajuela, Costa Rica

[21] Appl. No.: 422,534

[22] Filed: Apr. 14, 1995

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new and distinct Neoregelia named 'Nonis,' particularly characterized by its small plant size, bright red-purple center (R.H.S. 57A), leaf margins that are dark green (R.H.S. 137A) and a variegated center to the leaf.

3 Drawing Sheets

1

The present invention comprises a new and distinctive cultivar of Neoregelia hybrid, hereinafter referred to by the cultivar name 'Nonis.' Neoregelia species are tank epiphytes with stemless inflorescences and flowers that barely rise above the water in the center of plants. 'Nonis' can be advantageously grown as a single pot plant in order to display its symmetrically rosette plant form.

The new cultivar is a product of a planned breeding program, and was originated from a cross made during such a program in Balsa, Costa Rica in 1989. The female, or seed parent was *Neoregelia carolinae*×*Neoregelia compacta*. The male, or pollen parent was Neoregelia 'Fireball,' an unnamed species from Brazil known as *Neoregelia schultesiana* in Europe.

'Nonis' was discovered and selected as a flowering plant within the progeny of the stated cross by Chester Skotak, Jr. in 1991 in a controlled environment in Balsa, Costa Rica. Subsequent asexual reproduction by vegetative propagation has demonstrated that the combination of characteristics as herein disclosed for the new cultivar are firmly fixed and are retained through successive generations of asexual reproduction.

The new cultivar has not been observed under all possible environmental conditions. The phenotype may vary with variations in environment such as temperature, light, intensity and day length, without any variation in the genotpe of the plant.

The following traits have been repeatedly observed and are determined to be basic characteristics of 'Nonis' that in combination distinguish this Neoregelia as a new and distinct cultivar:

1. 'Nonis' is small in size measuring 20 to 24 cm in height when grown in 12.5 cm pots and approximately 30 cm in diameter when fully grown.

2. 'Nonis' has a rich red center color because the basal portion of the innermost leaves is red-purple (R.H.S. 57A).

3. The margins of the leaves are dark green (R.H.S. 137A) with a variegated center.

The following observations, measurements and values describe plants grown in Balsa, Cosa Rico and Goulds, Fla., U.S.A. under greenhouse conditions which closely approximate those generally used in horticultural practice. Color references are made to The Royal Horticultural Society (R.H.S.) Colour Chart, except where general color terms of ordinary significance are used. The color values were determined at approximately 3:30 p.m. on Apr. 11, 1995 under natural light in Washington, D.C., U.S.A.

The new cultivar can be compared to Neoregelia 'Fireball.' 'Nonis' is variegated in the center of the leaf unlike 'Fireball.' In addition, the leaf color in the center of 'Nonis' is more intense than 'Fireball.'

2

The accompanying photographic drawings show typical characteristics of the new cultivar with colors being as true as possible with illustrations of this type.

Sheet 1 is a side view of the plant.

Sheet 2 is a top view of the plant.

Sheet 3 is a closeup of the plant center showing the flowers.

Classification:

*Botanical.*—Neoregelia hybrid, cv. 'Nonis'.

*Commercial.*—Neoregelia 'Nonis'.

Parenage:

*Male parent.*—Neoregelia 'Fireball'.

*Female parent.*—*Neoregelia carolinae.*

Propagation: Asexual by means of offset removal.

Plant description: From 20 cm to 24 cm tall when grown in 12.5 cm pots and approximately 30 cm in diameter when fully grown.

*Growth habit.*—Small spreading rosette.

Leaves:

*Form.*—Blades lingulate, broadly rounded and blunt with finely serrated margins.

*Size.*—Length: 14 to 16 cm. Width: 2 cm at tip and 3.5 to 4 cm in middle.

*Texture.*—Smooth.

*Veins or ribs.*—None.

*Color* (R.H.S.).—Upper surface: The margin of the lear is dark green (R.H.S. 137A) and the center of the leaf is variegated. The basal portion of the innermost leaves is red-purple (R.H.S. 57A). Lower surface: Same as upper surface. Number of leaves: Average 12 to 16.

Flower:

*Arrangement.*—Deeply sunken small rosette

*Color.*—The apical portion is dark blue (R.H.S. 111A) and the basal portion is white.

*Fruit.*—White and ellipsoid measuring approximately 10 mm long.

*Duration of flowers.*—10 days to 2 weeks.

*Other significant characteristics.*—Bright colors.

Reproductive organs:

*Stamens.*—Pale yellow.

*Pistills.*—White. Ovary: Ellipsoid measuring approximately 10 mm long and 3 mm in diameter.

Resistance to disease: Disease resistant and very robust.

General observations: The unique small size is combined with a rich red center and variegated leaves.

I claim:

1. A new and distinct cultivar or Neoregelia plant named 'Nonis,' as illustrated and described.

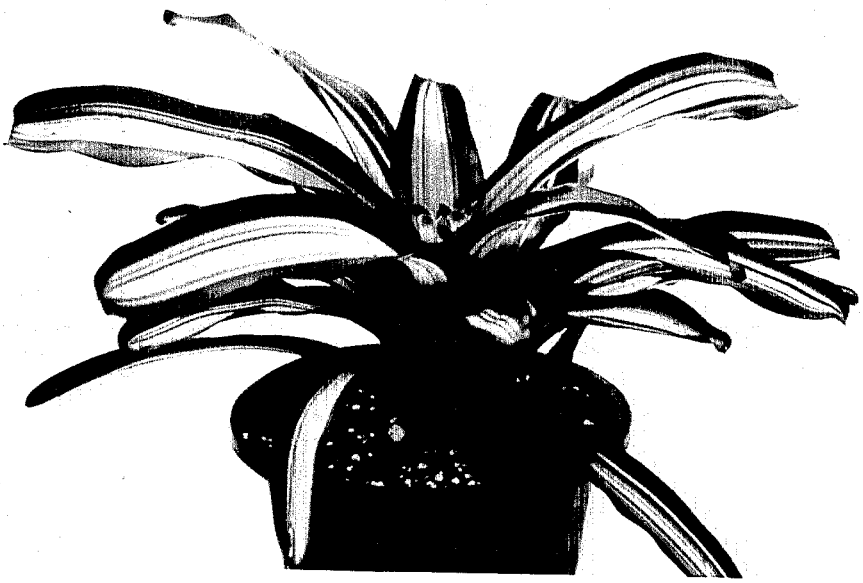

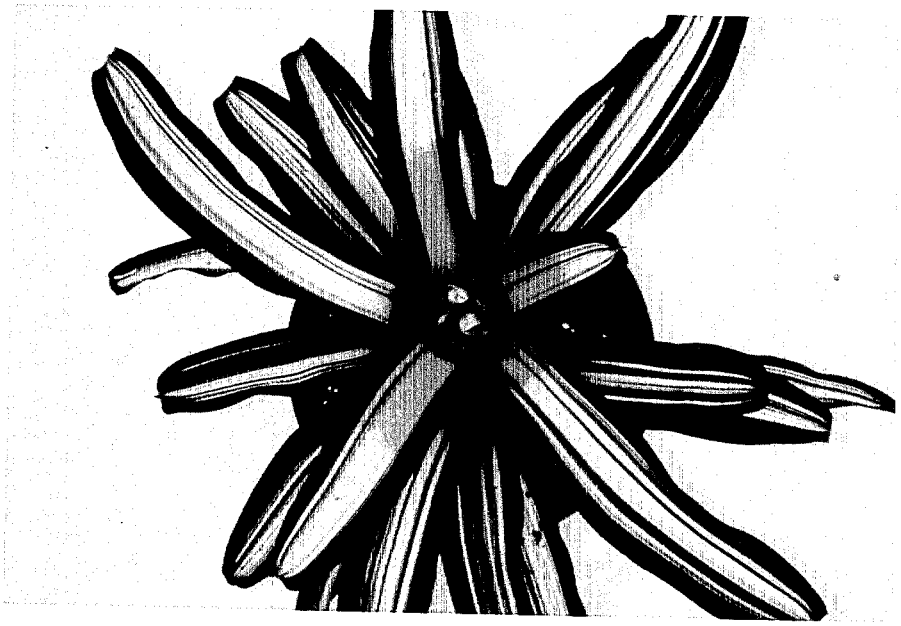

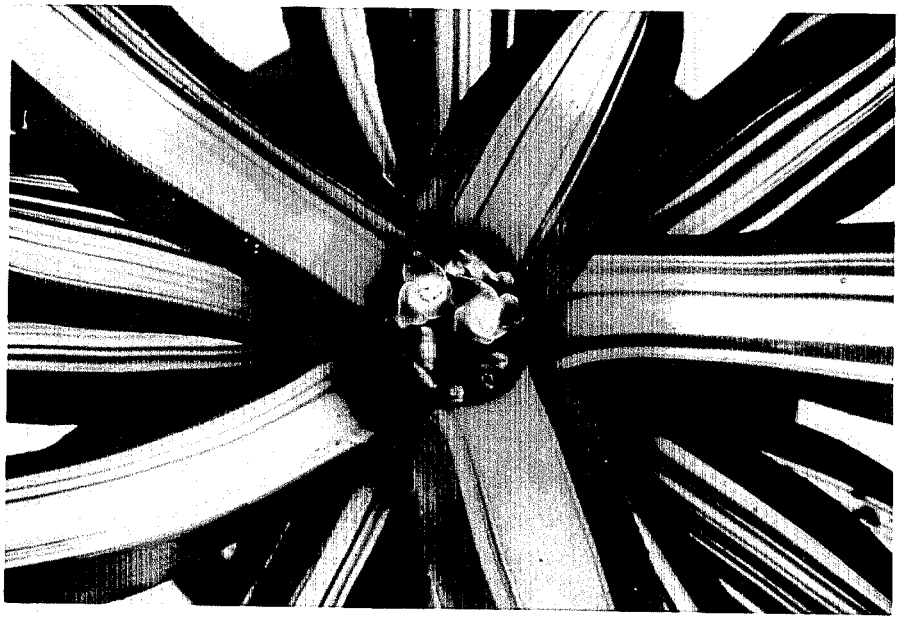

* * * * *